Figure 5:
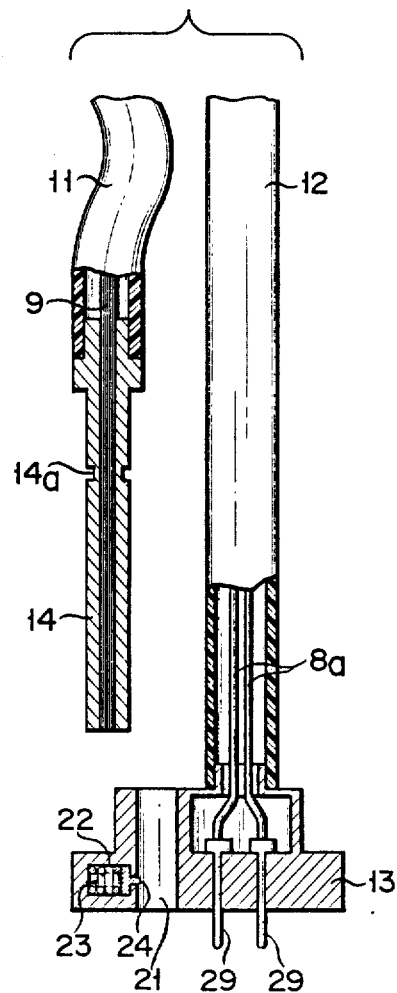

United States Patent [19]

Hagino

[11] 4,416,268
[45] Nov. 22, 1983

[54] ENDOSCOPE HAVING TWO DETACHABLE ARMOUR TUBES

[75] Inventor: Tadao Hagino, Yokohama, Japan

[73] Assignee: Olympus Optical Co., Ltd., Tokyo, Japan

[21] Appl. No.: 278,096

[22] Filed: Jun. 29, 1981

[30] Foreign Application Priority Data

Jul. 10, 1980 [JP] Japan .................. 55-94190
Sep. 30, 1980 [JP] Japan .................. 55-136127

[51] Int. Cl.³ ............................. A61B 1/06
[52] U.S. Cl. .................................... 128/6
[58] Field of Search ................ 128/6, 4, 7, 8, 9

[56] References Cited

U.S. PATENT DOCUMENTS

| | | | |
|---|---|---|---|
| 3,294,085 | 12/1966 | Wallace | 128/6 |
| 3,726,272 | 4/1973 | Fukami | 128/6 |
| 3,850,162 | 11/1974 | Iglesias | 128/6 |
| 4,190,041 | 2/1980 | Chikama | 128/6 |
| 4,261,345 | 4/1981 | Yamaguchi | 128/6 |
| 4,294,234 | 10/1981 | Matsuo | 128/6 |

FOREIGN PATENT DOCUMENTS 2738203 3/1979 Fed. Rep. of Germany ......... 128/6

*Primary Examiner*—Kyle L. Howell
*Assistant Examiner*—Max F. Hindenburg

[57] ABSTRACT

An endoscope comprises an endoscope body including a control section and an insert section, a first armour tube having one end connected with said control section, a light guide extending through said endoscope body and said first armour tube, a second armour tube having one end connected with said control section and separated from said first armour tube, a tube and/or conductors extending through said endoscope body and said second armour tube, and connector connected with the other ends of said first and second armour tubes for coupling said light guide and said insert means to a light source unit.

6 Claims, 11 Drawing Figures

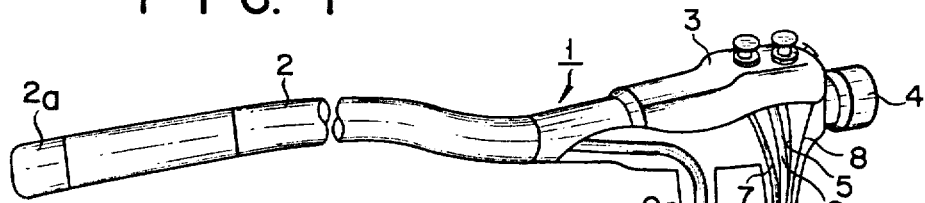
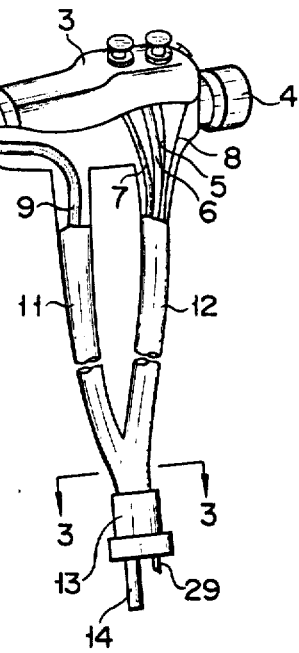
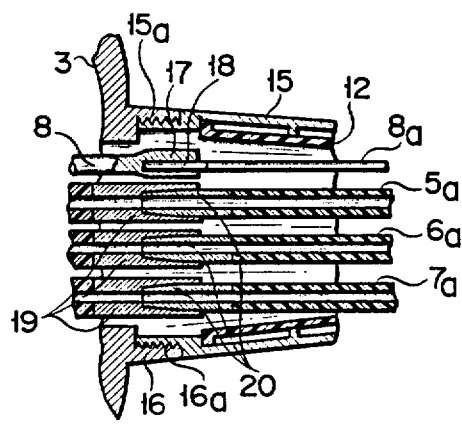
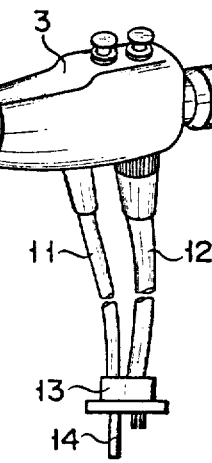
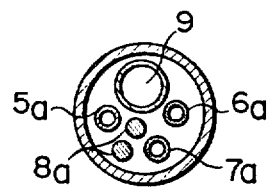

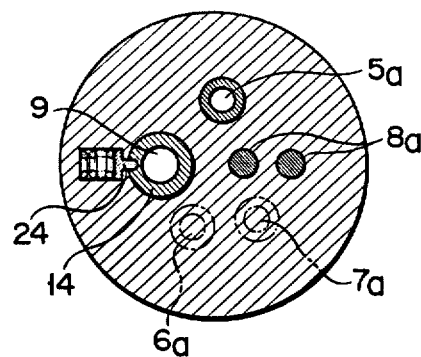
FIG. 7
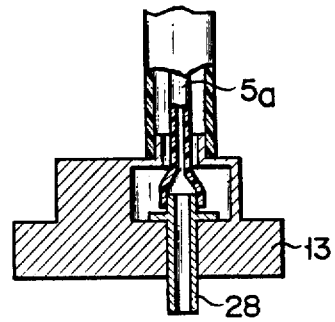
FIG. 8
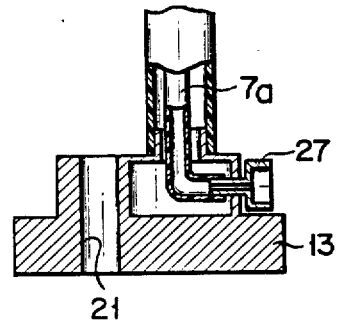
FIG. 9
FIG. 11
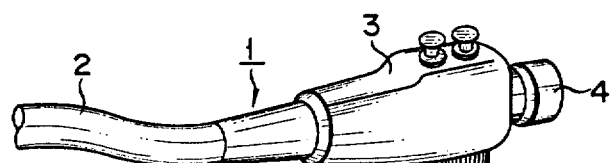
FIG. 10
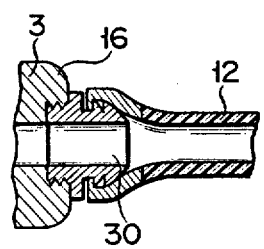
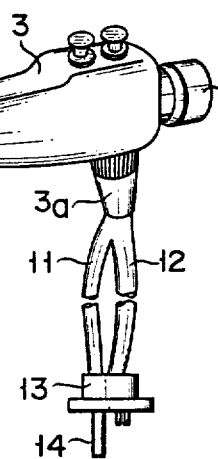

ENDOSCOPE HAVING TWO DETACHABLE ARMOUR TUBES

This invention relates to an endoscope which, in use, is connected with a light source unit.

In general, an endoscope contains therein various members including a light guide, air feed tube, water feed tube and conductors, as well as an image guide, which are connected with a light source unit. Conventionally, all these insert members are collectively inserted in a single universal cord led out of the control section of the endoscope body, and the respective distal ends of the insert members extend to a connector fitted on the distal end of the universal cord. The connector may be removably attached to the socket of the light source unit, and the insert members are connected with their corresponding source means including an electric power source, light source, air supply source, water source, etc. when the connector is attached to the socket.

Where all the insert members connected with the light source unit are inserted in the single universal cord, however, they need be thoroughly disjointed from one another for repair if any of those members, such as conductors or tubes, which are liable to be broken or clogged goes wrong. Thus, such construction would require very troublesome repair work.

The object of this invention is to provide an endoscope capable of easy repair without exerting any bad influence upon the light guide in case of breakage or clogging of any insert member connected with the light source unit, or upon a specific insert member or members in case of the light guide becoming defective due to breakage or the like.

In an endoscope of this invention, an armour tube is divided into first and second armour tubes in which a light guide and elongated insert section consisting of at least one tube and/or conductor are inserted respectively, the light guide and insert section extending from a control section and connected with a light source unit.

According to a preferred embodiment of the invention, the second armour tube containing the insert means is removably attached to the main body of the endoscope.

As for the first armour tube containing the light guide, it is removably attached to a connector for connecting the tube with the light source unit.

Figure 6:
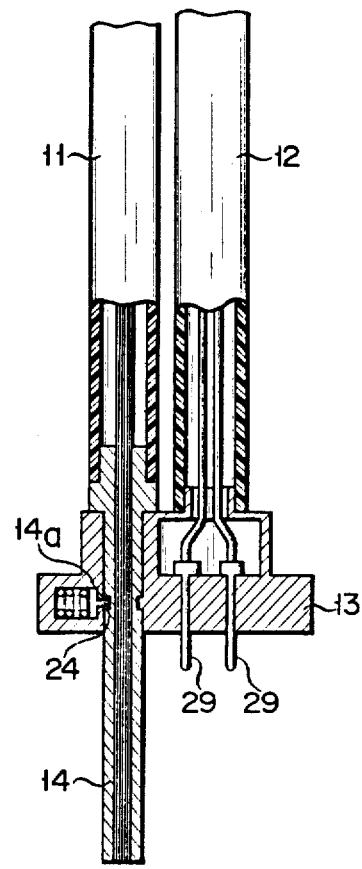

This invention can be more fully understood from the following detailed description when taken in conjunction with the accompanying drawings, in which:

FIGS. 1 to 3 shows an endoscope according to one embodiment of this invention, in which FIG. 1 is a broken away, general perspective view of the endoscope, FIG. 2 is a sectional view showing the junction of a control section and a second armour tube, and FIG. 3 is a sectional view taken along line 3—3 of FIG. 1;

FIGS. 4 to 9 show an endoscope according to the other embodiment of the invention, in which FIG. 4 is a perspective view schematically showing a part of the endoscope, FIGS. 5 and 6 are broken away, front views of armour tubes and a connector, showing different states where the first armour tube is removed from and fixed to the connector, respectively, FIG. 7 is a cross-sectional view of the connector, FIG. 8 is a broken away, front view showing the connector and an air feed tube, and FIG. 9 is a broken away, front view showing the connector and a suction tube;

FIG. 10 is a sectional view showing a modification of the junction of the control section and the second armour tube; and FIG. 11 is a schematic perspective view showing an endoscope of further embodiment.

Now there will be described an endoscope according to an embodiment of this invention with reference to the accompanying drawings.

In FIG. 1, numeral 1 designates the main body of the endoscope which is composed of an insert section 2 to be inserted into a body cavity, a control section 3 at the proximal end of the insert section 2 for externally performing various operations, and an eyepiece section 4 attached to the control section 3. A distal end 2a is attached to the tip of the insert section 2.

Inserted in the endoscope body 1 are tubes including an air feed tube 5, a water feed tube 6, and a suction tube 7, a conductor 8, and a light guide 9 utilizing an optical fiber bundle, as well as an image guide (not shown), so that their distal ends are all located at the distal end 2a, except that of the conductor 8 which is located at the eyepiece section 4 as mentioned later. As is generally known, the proximal end of the image guide is connected with the eyepiece section 4.

First and second armour tubes 11 and 12 are led out of the control section 3. In this embodiment, the first armour tube 11 is integrally connected with the control section 3, and the second armour tube 12 is removably connected with the control section 3 by a means mentioned later. The connection between these armour tubes and the control section is not, however, limited to such arrangements. The distal end portions of the armour tubes 11 and 12 are united together to form a common short tube which is connected with a connector 13. The connector 13 is designed by a well-known method so that it may be attached to and detached from the socket of a light source unit (not shown).

Inside the first armour tube 11, the light guide 9 extends from the endoscope body 1, having its tip end connected with a connector pin 14. The connector pin 14 is attached to the connector 13 with its tip end projected from the frontage of the connector 13.

Inserted in the second armour tube 12, as shown in FIGS. 2 and 3, are an air feed tube 5a, water feed tube 6a, suction tube 7a, and conductor 8a that are connected respectively with the air feed tube 5, water feed tube 6, suction tube 7, and conductor 8 in the endoscope body 1. As shown in FIG. 2, moreover, the proximal end of the second armour tube 12 is fitted with a mouthpiece 15 capable of axial movement and rotation relative to the armour tube 12. An external thread 15a is formed in the outer circumferential surface of the proximal end of the mouthpiece 15, while an internal thread 16a is formed in the inner circumferential surface of an insert member outlet port 16 of the control section 3. Thus, the second armour tube 12 is connected with the control section 3 by screwing the mouthpiece 15 into the outlet port 16. As shown in FIG. 2, the two conductors 8 and 8a are coupled by means of a pin socket 17 connected with one of the conductors and a pin 18 connected with the other. The first tubes 5, 6 and 7 and the second tubes 5a, 6a and 7a are coupled by means of mouthpiece sockets 19 connected with the former and mouthpieces 20 connected with the latter.

On the connector 13 side, the tip end of the conductor 8a is connected with a terminal pin 29, and may be electrically connected with a terminal attached to the socket of the light source unit. The conductor 8a is electrically connected with a photoelectric converting element (not shown) contained in the eyepiece section 4, and supplies an automatic exposure control circuit in the light source unit with a signal corresponding to the intensity of light received by the eyepiece section 4 at time of photographing, thereby performing automatic regulation of exposure. The distal end of the air feed tube 5a is projected from the distal end face of the connector 13, and the distal ends of the suction tube 7a and water feed tube 6a open on the circumferential side face of the connector 13. Thus, the distal ends of these tubes can be connected with their corresponding units.

In the device of the above-mentioned embodiment thus constructed, the light guide 9 is inserted in the first armour tube 11, the tubes 5a, 6a and 7a and the conductor 8a, which are relatively susceptible to trouble, are inserted in the second armour tube 12, and the first and second armour tubes 11 and 12 are separated from each other except their distal end portions. Accordingly, if the tube 5a, 6a or 7a is clogged or the conductor 8a is broken, the device of the invention can be disassembled for the ease of repair without exerting any influence upon the first armour tube 11. Further, the second armour tube 12, as well as the tubes 5a, 6a and 7a and the conductor 8a, is removably attached to the control section 3, so that a defective member or members can be easily removed to facilitate repair work without breaking the second armour tube 12. The two armour tubes may be formed of different materials with different thicknesses, depending on the flexibility and other properties of the members inserted therein.

Referring now to FIGS. 4 to 9, there will be described an endoscope according to the other embodiment of the invention.

In this embodiment, the first and second armour tubes 11 and 12 are entirely separated from each other, and the respective tip ends of these tubes are connected with the connector 13. Formed in the connector 13, as shown in FIG. 5, is a through hole 21 through which the connector pin 14 is passed. Also, the connector 13 is provided with a lateral hole 22 which opens into the through hole 21. The lateral hole 22 contains therein a compression spring 23 and an engaging pin 24 which is urged by the spring 23 so that its tips end projects into the through hole 21. An annular engaging recess 14a is formed in the circumferential side face of the connector pin 14 connected with the light guide 9. Thus, the connector pin 14 is fixed to the connector 13, as shown in FIG. 6, by passing the connector pin 14 through the hole 21 of the connector 13 so that the engaging pin 24 is forced into the engaging recess 14a. If the connector pin 14 is pulled back strongly, on the other hand, the engaging pin 24 is released from the engagement with the recess 14a so that the connector pin 14 can be removed from the connector 13, as shown in FIG. 5.

The air feed tube 5a, water feed tube 6a, suction tube 7a, and conductor 8a inserted in the second armour tube 12 are connected with the connector 13 in the same manner as the foregoing embodiment. Namely, the conductor 8a is connected with a contact pin 29 which is fixed to the connector 13 so as to be projected from the frontage of the connector 13. As shown in FIG. 8, the air feed tube 5a is coupled with an air feed pipe 28 which is fixed to the connector 13 so that its distal end portion is projected from the connector 13. As shown in FIG. 9, the suction tube 7a is connected with a suction port 27 penetratingly fixed to the outer peripheral wall of the connector 13, and, in this embodiment, is allowed to communicate with a suction unit provided separately from the light source unit. Although not shown in FIG. 8, the water feed tube 6a is connected with the connector 13 in the same manner as the suction tube 6a.

Although firmly attached to the connector in the above embodiment, the second armour tube 12 may be constructed so as to be able to be easily removed from the connector.

The second armour tube 12 and the control section 3 may be connected by means of a coupling member 30 having an external thread on the outer peripheral surface of one end thereof mating with an internal thread formed on the mouthpiece of the second armour tube 12, and another external thread on the outer peripheral surface of the other end thereof on the port 16 of the control section, as shown in FIG. 10. Alternatively, the control section 3 and the second armour tube 12 may be connected by any other suitable means than screwing, such as e.g. press fit means, beyonet coupling means, etc.

Besides the light guide, some other suitable insert members, such as conductors, may be inserted in the first armour tube.

FIG. 11 shows an endoscope of further embodiment in which the control section 3 is provided with a projecting section 3a. The projecting section 3a and control section 3 may be separately formed and connected with each other, or may be integrally formed. The control section 3a may be made to have a flexibility.

What is claimed is:

1. An endoscope coupled with a light source unit, comprising:
    an endoscope body including a control section and an insert section;
    a first armour tube having one end connected with said control section;
    a light source;
    a light guide extending from said light source and through said endoscope body, alone and only through said first armour tube;
    a second armour tube having one end connected with said control section and separated from said first armour tube up to about the distal end portions of each said tube;
    an elongated insert means extending from said endoscope body and said second armour tube and terminating at the distal end thereof to be inserted into a body cavity;
    first coupling means connecting the ends of said first and second armour tubes to said control section for coupling said light guide and said insert means to the light source unit; and
    a second removable coupling means for connecting said first and second armour tubes to a light source and sources of water, air, and suction, said coupling means including a hole formed therein through which the said first armour tube is inserted, an engaging pin having a tip extendable into the through hole, a spring urging the engaging pin into the through hole, and a recess formed in the face of the first armour tube adapted to engage the tip of the engaging pin to firmly position the first armour tube with respect to said coupling means.

2. An endoscope according to claim 1, wherein said insert means includes at least one tube.

3. An endoscope according to claim 2, wherein said insert means includes at least one conductor for providing the distal end of the endoscope, with the necessary means to perform its functions.

4. An endoscope according to claim 3, wherein said insert means includes an air feed tube, a water feed tube, and a suction tube.

5. An endoscope according to claim 1, further comprising first coupling means for removably connecting said second armour tube with said control section.

6. An endoscope according to claim 5, wherein said first coupling means includes a mouthpiece attached to said second armour tube so as to be able to rotate and move in the axial direction of said second armour tube and having a first screw portion, and a second screw portion formed on said control section and capable of mating with said first screw portion.

* * * * *